United States Patent [19]

Mieno et al.

[11] Patent Number: 4,873,642

[45] Date of Patent: Oct. 10, 1989

[54] METHOD FOR CONTROLLING AN OXYGEN CONCENTRATION SENSOR FOR USE IN AN AIR/FUEL RATIO CONTROL SYSTEM OF AN INTERNAL COMBUSTION ENGINE

[75] Inventors: Toshiyuki Mieno; Toyohei Nakajima; Yasushi Okada; Nobuyuki Oono, all of Wako, Japan

[73] Assignee: Honda Giken Kogyo Kabushiki Kaisha, Tokyo, Japan

[21] Appl. No.: 21,704

[22] Filed: Mar. 4, 1987

[30] Foreign Application Priority Data

Mar. 4, 1986 [JP] Japan .................................. 61-47547

[51] Int. Cl.$^4$ ........................ F02M 51/00; F02M 7/00
[52] U.S. Cl. ............................ 364/431.06; 364/431.05; 123/489; 123/440
[58] Field of Search ....................... 164/431.05, 431.06; 123/440, 489, 589; 204/14, 406, 412, 425, 426; 364/431.03, 431.04

[56] References Cited

U.S. PATENT DOCUMENTS

| | | | |
|---|---|---|---|
| 4,332,225 | 6/1982 | Cox et al. | 123/440 |
| 4,365,604 | 12/1982 | Sone | 123/440 |
| 4,538,575 | 9/1985 | Chujo et al. | 123/440 |
| 4,541,899 | 9/1985 | Mase et al. | 204/424 |
| 4,541,900 | 9/1985 | Mase et al. | 204/424 |
| 4,658,790 | 4/1987 | Hitahara | 123/489 |
| 4,665,874 | 5/1987 | Kawanabe et al. | 123/440 |
| 4,698,209 | 10/1987 | Hashimoto et al. | 123/489 |
| 4,719,895 | 1/1988 | Mieno et al. | 123/589 |
| 4,721,084 | 1/1988 | Kawanabe et al. | 123/489 |
| 4,721,088 | 1/1988 | Mieno et al. | 123/489 |

FOREIGN PATENT DOCUMENTS

| | | | |
|---|---|---|---|
| 0216254 | 10/1985 | Japan | 364/431.05 |
| 0216255 | 10/1985 | Japan | 364/431.05 |
| 0235047 | 11/1985 | Japan | 364/431.05 |
| 0235048 | 11/1985 | Japan | 364/431.05 |
| 0235049 | 11/1985 | Japan | 364/431.05 |
| 0235050 | 11/1985 | Japan | 364/431.05 |

*Primary Examiner*—Parshotam S. Lall
*Assistant Examiner*—V. N. Trans
*Attorney, Agent, or Firm*—Birch, Stewart, Kolasch & Birch

[57] ABSTRACT

A method for controlling an oxygen concentration sensor for controlling an internal combustion engine, having a sensor body including a wall of oxygen ion conductive solid electrolyte member, and a heater element for heating the wall of oxygen ion conductive solid electrolyte member. During a time period after the ignition switch of the internal combustion engine is turned on, current value of the heater current to the heater element is reduced to a value which is smaller than the current value of the heater current to be supplied after the lapse of the time period.

4 Claims, 6 Drawing Sheets

TO STEP 68

METHOD FOR CONTROLLING AN OXYGEN CONCENTRATION SENSOR FOR USE IN AN AIR/FUEL RATIO CONTROL SYSTEM OF AN INTERNAL COMBUSTION ENGINE

BACKGROUND OF THE INVENTION

1. Field of the Invention

The present invention relates to a method for controlling an oxygen concentration sensor for use in an air/fuel ratio control system of an internal combustion engine.

2. Description of Backgroud Information

Systems for controlling the air/fuel ratio by feedback operation have been developed, in which oxygen concentration in the exhaust gas of the engine is detected by an oxygen concentration sensor and the air/fuel ratio of mixture to be supplied to the engine is controlled using a feedback method to a target value in response to an output signal level from the $O_2$ sensor for the purpose of purifying of the exhaust gas and improving of the fuel economy.

As an oxygen concentration sensor for use in such an air/fuel ratio control system, there is a type which is capable of producing an output signal whose level is proportional to the oxygen concentration in the exhaust gas of the engine. For example, a critical current type oxygen concentration sensor which includes a flat oxygen ion conductive solid electrolyte member provided with a pair of electrodes on both of its main surfaces. The surface of one of the electrodes forms a part of a gas retaining chamber. This gas retaining chamber communicates with a flow of measuring gas such as the exhaust gas through a communication hole. This oxygen sensor is disclosed in Japanese Patent Application laid open No. 52-72286. In this oxygen concentration sensor, the oxygen ion conductive solid electrolyte member and the electrode pair serve as an oxygen pump element. If a current is supplied to the electrodes in such a manner that the electrodes facing the gas retaining chamber operates as a negative electrode, the oxygen component of the gas in the gas retaining chamber is ionized on the surface of the negative electrode of the oxygen pump element, and migrates through the inside of the oxygen pump element to the positive electrode where the oxygen ions are released from the surface in the form of the oxygen gas.

Under this condition, the magnitude of the critical current flowing through the electrodes becomes constant irrespective of the applied voltage but varies substantially in proportion to the oxygen concentration in the measuring gas. Therefore, by detecting the critical current value, the oxygen concentration in the measuring gas can be measured. However, if the air/fuel ratio is controlled by using this oxygen concentration sensor, the output signal from the oxygen concentration sensor becomes proportional to the oxygen concentration only when the air/fuel ratio of the mixture supplied to the engine is leaner than the stoichiometric air/fuel ratio. Therefore, an air/fuel ratio control operation using a target air/fuel ratio which is set in a rich range is not possible. As an example of oxygen concentration sensor capable of producing an output signal which is proportional to the oxygen concentration in the exhaust gas in both of the lean and rich ranges, the oxygen concentration sensor will include a pair of flat oxygen ion conductive solid electrolyte members each of which is provided with a pair of electrodes. The surface of one electrode of each solid electrolyte member forms a part of a gas retaining chamber which gas retaining chamber communicates with a flow of measuring gas through a communication hole. The surface of the other electrode of one of two solid electrolyte members faces an atmospheric chamber. This oxygen concentration sensor is disclosed in Japanese Patent Application laid open No. 59-192955. In this oxygen concentration sensor, one of two oxygen ion conductive solid electrolyte members and its electrode pair serve as an oxygen concentration ratio detection sensor cell element, and the other one of two oxygen ion conductive solid electrolyte members and its electrode pair serve as the oxygen pump element. By supplying a current so that the oxygen ions moves through the inside of the oxygen pump element toward the electrode located on the gas retaining chamber's side when the voltage generated across the electrodes of the oxygen concentration ratio detection sensor cell element is higher than a reference voltage, and so that the oxygen ions move through the inside of the oxygen pump element toward the electrode located on the other side of the gas retaining chamber when the voltage generated across the oxygen concentration ratio detection sensor cell element is equal to or lower than the reference voltage, the current value becomes proportional to the oxygen concentration both in the lean and rich regions.

In the case of this oxygen concentration proportional type oxygen concentration sensor, the temperature of the sensor must be sufficiently higher than (higher than 650° C., for example) the temperature of the exhaust gas under a steady condition of the engine operation in order to obtain an oxygen concentration proportional type output signal characteristic. For this reason, a heater element is incorporated in the oxygen concentration sensor, to heat the oxygen pump element and sensor cell element. When the engine is started, the oxygen pump element and the sensor cell element must be heated by the heater element, to activate the oxygen concentration sensor quickly so that the feedback control of air/fuel ratio can begin.

However, the problem encountered in the conventional technique is that the oxygen pump element and the sensor cell element can be damaged by thermal shock if the oxygen pump element and the sensor cell element are heated rapidly by the supply of a heater current to the heater element during the time of a cold start of the engine.

OBJECTIVES AND SUMMARY OF THE INVENTION

An objective of the present invention is therefore to provide a method for controlling an oxygen concentration sensor by which the oxygen pump element and the sensor cell element are prevented from being damaged by the heat of the heater element, and which enables the start of the feedback control of the air/fuel ratio shortly after the closure of the ignition switch.

According to the present invention, a method for controlling an oxygen concentration sensor for controlling an internal combustion engine having an ignition switch and an exhaust gas passage, the oxygen concentration sensor including, a sensor body forming a gas retaining space which communicates with an inside of the exhaust gas passage through a gas diffusion restriction region, and which includes a wall of oxygen ion conductive solid electrolyte member, two pairs of electrodes, each pair of which is disposed on opposing sides of the wall of oxygen ion conductive solid electrolyte member, and a current source for supplying a current, in response to a difference between a voltage developing across one pair electrodes of the two pairs of electrodes and a reference voltage, across the other pair electrodes of the two pairs of electrodes, and a heater element for generating heat for heating the wall of oxygen ion conductive solid electrolyte member in accordance with the amount of a heater current supplied thereto, the method comprising steps of:

measuring time lapsed after the ignition switch of the internal combustion engine is turned on; and controlling a current value of the heater current, during a first predetermined time period after the ignition switch is turned on, to be smaller than the current value of the heater current to be supplied to the heater element after a lapse of the first predetermined time period.

In short, according to a first aspect of the present invention, the method for controlling an oxygen concentration sensor is characterized by reducing the value of current to the heater element during a first predetermined time period after the ignition switch is turned on a value lower than the current being supplied to the heater element after the lapse of the first predetermined time period.

According to another aspect of the present invention, a method for controlling an oxygen concentration sensor further comprises a step for controlling the current source of the oxygen concentration sensor to start the supply of the current to the other pair electrodes when a second predetermined time period has lapsed after the lapse of the first predetermined time period.

According to further aspect of the present invention, a method for controlling an oxygen concentration sensor for controlling an internal combustion engine having an ignition switch and an exhaust gas passage, the oxygen concentration sensor including, a sensor body forming a gas retaining space which communicates with an inside of the exhaust gas passage through a gas diffusion restriction region, and which includes a wall of oxygen ion conductive solid electrolyte member, two pairs of electrodes, each pair of which is disposed on opposing sides of the wall of oxygen ion conductive solid electrolyte member, and a current source for supplying a current, in response to a difference between a voltage developing across one pair electrodes of the two pairs of electrodes and a reference voltage, across the other pair electrodes of the two pairs of electrodes, and a heater element for generating heat for heating the wall of oxygen ion conductive solid electrolyte member in accordance with the amount of a heater current supplied thereto, the method comprising steps of:

detecting an operational state of the internal combustion engine; and controlling a current value of the heater current, until the operational state of the internal combustion engine detected by the detecting step reaches a predetermined operational state after the ignition switch of the internal combustion engine is turned on, to be smaller than the current value of the heater current to be supplied to the heater element after the predetermined operational state is reached.

In short, according to a third aspect of the present invention, the method for controlling an oxygen concentration sensor is characterized by reducing the value of current to the heater element until a predetermined operational state of the engine is reached after the ignition switch is turned on, to be lower than the value of the current to the heater element to be supplied after the predetermined operational state of the engine is reached.

According to still further aspect of the present invention, the predetermined operational state is an operational state of the internal combustion engine in which a rotational speed of the internal combustion engine is raised to be higher than a predetermined rotational speed.

DETAILED DESCRIPTION OF A PREFERRED EMBODIMENT

Referring to the accompanying drawings, an embodiment of the present invention will be explained below.

Figure 1:
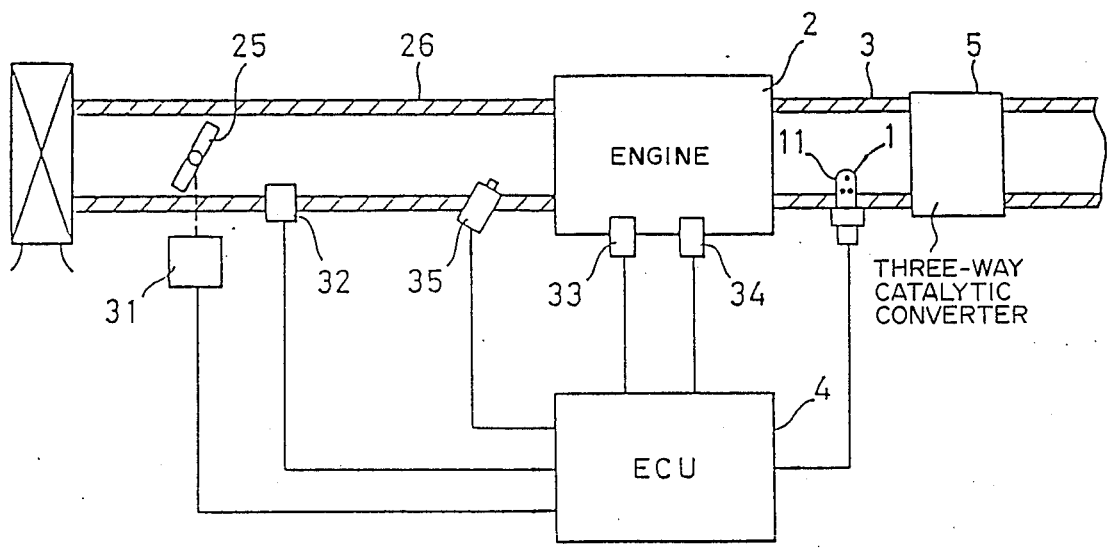
FIG. 1 is a schematic diagram showing a general construction of a fuel injection system in which the method for controlling an oxygen concentration sensor according to the invention is applied.
Figure 2:
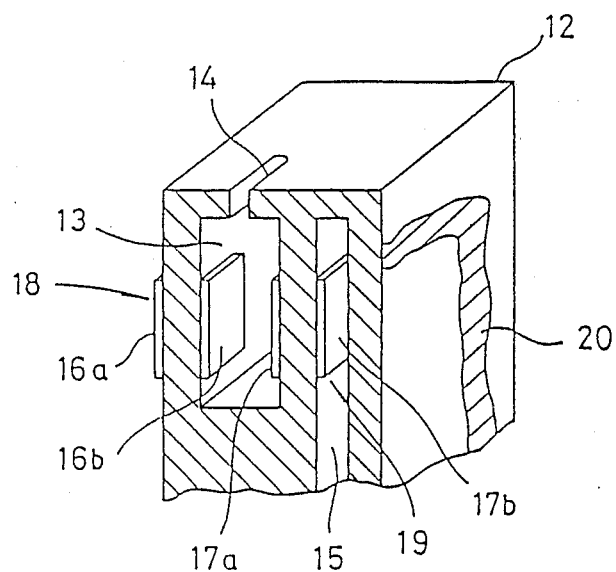
FIG. 2 is a diagram showing an inside of the detection part of the oxygen concentration sensor used in the system of FIG. 1.
Figure 3:
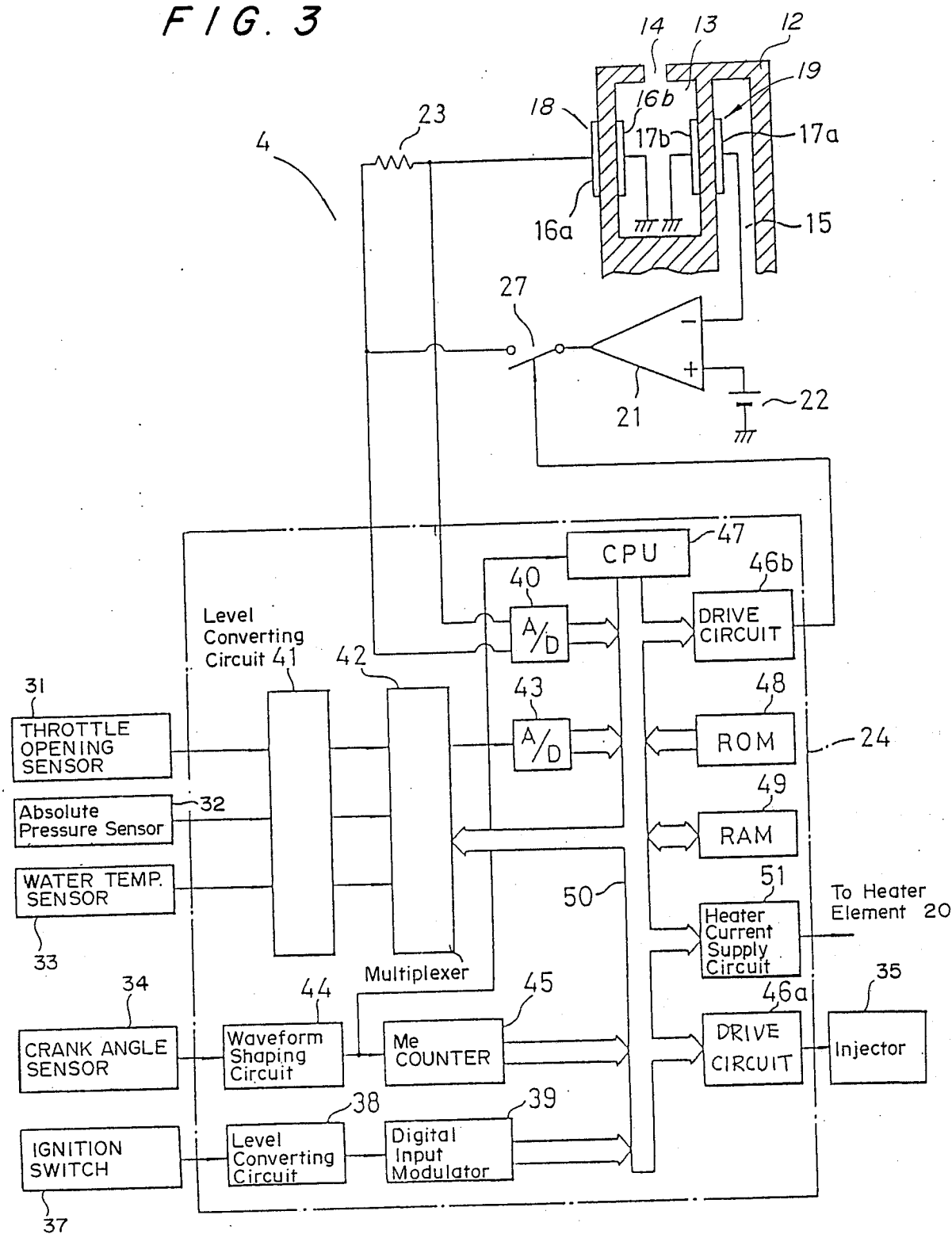
FIG. 3 is a block diagram showing the circuit construction of the ECU 4 of the system of FIG. 1.

FIGS. 1 through 3 illustrate an electronically controlled fuel injection system of an internal combustion engine equipped with an oxygen concentration sensor to which the control method of the present invention is applied. In this system, an oxygen concentration sensor is utilized, and a detection part 1 of the oxygen concentration sensor is disposed in an exhaust gas passage 3 of an engine 2, on the upstream side of a three-way catalytic converter 5. Input and output signals from the detection part 1 of the oxygen concentration sensor are supplied to an ECU (electronic control unit) 4.

In a protection case 11 of the detection part 1 of the oxygen concentration sensor, there is provided an oxygen ion conductive solid electrolyte member 12 having a general configuration of a rectangular parallelepiped, as shown in FIG. 2. In the oxygen ion conductive solid electrolyte member 12, a gas retaining chamber 13 is provided. The gas retaining chamber 13 leads to a gas introduction hole 14 for introducing the measuring gas, i.e. the exhaust gas of the engine, from outside of the oxigen ion conductive solid electrolyte member 12. The gas introduction hole 14 is positioned in an exhaust gas passage 3 so that the exhaust gas can easily flow into the gas retaining chamber 13. The gas introduction hole 14 functions as a gas diffusion restriction region. The oxygen-ion conductive solid electrolyte member 12 is provided with a reference atmospheric air chamber 15 into which atmospheric air is introduced, in such a manner that the reference atmospheric air chamber 15 is separated from the gas retaining chambers 13 by means of a partition wall between them. On the partition wall between the gas retaining chamber 13 and the reference atmospheric air chamber 15, and on the wall of the gas retaining chamber 13 on the opposite side of the atmospheric air chamber 15, there are respectively a pair of electrodes 17a and 17b and a pair of electrodes 16a and 16b. The solid electrolyte member 12 and the pair of electrodes 16a and 16b operate together as an oxygen pump element 18. On the other hand, the solid electrolyte member 12 and the pair of electrodes 17a and 17b operate together as a sensor cell element 19. Further, a heater element 20 is provided on an outer wall of the reference atmospheric air chamber 15. For the oxygen ion conductive solid electrolyte 12, zirconium dioxide ($ZrO_2$) is suitably used, and platinum (Pt) is used for the electrodes 16a through 17b.

As shown in FIG. 3, the ECU 4 includes a differential amplifier 21, a reference voltage source 22, a current detection resistor 23, an oxygen concentration sensor control part which comprises a switch 27 and a control circuit 24. The electrode 16b of the oxygen pump element 18 and the electrode 17b of the sensor cell element 19 are grounded. The differential amplifier 21 is connected to the electrode 17a of the sensor cell element 19, and the differential amplifier 21 produces an output voltage corresponding to the difference between a voltage generated across the electrodes 17a and 17b of the sensor cell element 19 and a voltage generated by the reference voltage source 22. An output voltage of the reference voltage source 22 has a level (0.4 V for example) corresponding to the stoichiometric air/fuel ratio. An output terminal of the differential amplifier 21 is connected to the electrode 16a of the oxygen pump element 18 through the switch 27 and current detection resistor 23. Terminals of the current detection resistor 23 operate as output terminals of the oxygen concentration sensor, and are connected to the control circuit 24 which includes a microcomputer.

The air/fuel ratio control circuit 24 is connected to, a throttle opening sensor 31 which includes a potentiometer and generates an output voltage whose level corresponds to the opening of a throttle valve 25; an absolute pressure sensor 32 which is provided in an intake pipe 26 on the downstream side of the throttle valve 25 and generates an output signal whose level corresponds to the absolute pressure in the intake pipe 26; a cooling water temperature sensor 33 for generating an output voltage whose level corresponds to the cooling water temperature of the engine; a crank angle sensor 34 for generating a pulse train signal in synchronism with the rotation of the crankshaft (not shown) of the engine 2; and an ignition switch 37. The ignition switch 37 operates to supply an output voltage of a battery (not shown) to the control circuit 24 when it is turned on (closed). An injector 35 provided in an intake pipe 26 of the engine 2, near intake valves (not shown), is also connected to the control circuit 24.

The control circuit 24 includes, an A/D converter 40 having differential inputs which converts the voltage across the terminals of the current detection resistor 23 to a digital signal; a level converting circuit 41 for performing the level conversion of the output signals from the throttle opening sensor 31, the absolute pressure sensor 32, and the water temperature sensor 33; a multiplexer 42 for selectively outputting one of the output signals from the sensors through the level converting circuit 41; an A/D converter 43 for converting the signal supplied from the multiplexer 42 into a digital signal; a waveform shaping circuit 44 for performing the waveform shaping of the output signal from the crank angle sensor 34 and outputting it as a TDC signal; a counter 45 for detecting the period of the TDC signal by counting the number of clock pulses supplied from a clock pulse generating circuit (not shown); a level converting circuit 38 for converting an output signal from the ignition switch 37; a digital input modulator 39 for providing the output signal from the ignition switch from the level converting circuit 38 into digital data; a drive circuit 46a for driving the injector 35; a drive circuit 46b for driving the switch 27 to the "on" position; a CPU (central processing unit) 47 for executing digital operations according to programs; a ROM 48 in which various operation programs and data are previously stored; and a RAM 49. The A/D converters 40 and 43, the multiplexer 42, the counter 45, digital input modulator 39, the drive circuits 46a and 46b, the CPU 47, the ROM 48, and the RAM 49 are mutually connected by means of an input/output bus 50. Further, a heater current supply circuit 51 is provided in the control circuit 24. The heater current supply circuit 51 supplies a heater current having a current value of $I_{H1}$ to the heater element 20 in accordance with a first heater current supply command from the CPU 47. The heater current supply circuit 51 also supplies a heater current having a current value of $I_{H2}$ ($I_{H2} > I_{H1}$ to the heater element 20 in accordance with a second heater current supply command from the CPU 47. Further, the heater current supply circuit 51 stops the supply of the heater current in accordance with a heater current supply stop command from the CPU 47. The current values $I_{H1}$ and $I_{H2}$ are attained, for example, by varying the voltage of the heater current supplied to the heater element 20.

With this construction, data indicative of a pump currents $I_P$ flowing through the oxygen pump element 18 from the A/D converter 40; data of the throttle opening $\theta th$, the absolute pressure $P_{BA}$ in the intake pipe, and the cooling water temperature $T_W$ selectively from the A/D converter 43; information of the engine rotational speed Ne from the counter 45; and information of on-off state of the ignition switch 37 from the digital input modulator 39; are supplied to the CPU 47 through the input/output bus 50. The CPU 47 reads the various above-mentioned pieces of information in accordance with the program stored in the ROM 48 and calculates a fuel injection time $T_{OUT}$ of the injector 35 corresponding to the amount of the fuel to be supplied to the engine 2 using a calculation formula described below, in accordance with the red information and in synchronism with the TDC signal in a fuel supply routine. The fuel injector 35 is actuated by the drive circuit 46a only for the fuel injection time $T_{OUT}$ so as to supply the fuel to the engine 2.

The fuel injection time $T_{OUT}$ is, for example, calculated by the following formula:

$$T_{OUT} = T_i \times K_{O2} \times K_{WOT} \times K_{TW} \qquad (1)$$

where, $T_i$ represents a basic supply amount determined by the engine rotational speed Ne and the pressure $P_{BA}$ in the intake passage; $K_{O2}$ represents a feedback correction coefficient of the air/fuel ratio which is determined in accordance with the output signal level of the oxygen concentration sensor; $K_{WOT}$ represents a fuel increment correction coefficient for a high load operation; $K_{TW}$ represents a coefficient of the engine coolant temperature. The correction coefficients of $K_{O2}$, $K_{WOT}$, and $K_{TW}$ are set in subroutines of the fuel supply routine.

On the other hand, the drive circuit 46b drives the switch 27 to the "on" position in accordance with an "on" drive command from the CPU 47 and stops the driving of the switch 27 to the "on" position in accordance with an "on" drive halt command from the CPU 47. When the switch 27 is driven to the "on" position, a pump current from the output terminal of the differential amplifier 21 starts to flow across the electrodes 16a and 16b of the oxygen pump element 18 through the switch 27 and the resistor 23.

When the supply of the pump current to the oxygen pump element 18 is started, a voltage developing across the electrodes 17a and 17b of the sensor cell element 19 becomes lower than the voltage of the output signal from the reference voltage source 22 if the air/fuel ratio of the mixture supplied to the engine 2 is in the lean region. Therefore, the differential amplifier 21 produces a positive output signal. This positive output signal is supplied to the series circuit of the resistor 23 and the oxygen pump element 18. Since the pump current flows from the electrode 16a to the electrode 16b of the oxygen pump element 18, oxygen in the gas retaining chamber 13 is ionized at the electrode 16b, and moves through the inside of the oxygen pump element 18 and is released in the form of oxygen gas at the electrode 16a. The oxygen in the gas retaining chamber 13 is pumped out in this way.

By pumping the oxygen in the gas retaining chamber 13, a difference of oxygen concentration develops between the exhaust gas in the gas retaining chamber 13 and the atmospheric air in the reference atmospheric air chamber 15. A voltage Vs corresponding to this difference of oxygen concentration develops across the electrodes 17a and 17b of the sensor cell element 19. This voltage Vs is supplied to the inverting input terminal of the differential amplifier 21. Since the output voltage of the differential amplifier 21 becomes a voltage proportional to the difference between the voltage Vs and the voltage from the output signal of the reference voltage source 22, the pump current value becomes proportional to the oxygen concentration in the exhaust gas. This pump current value is outputted as a voltage across the terminals of the resistor 23.

Figure 4:
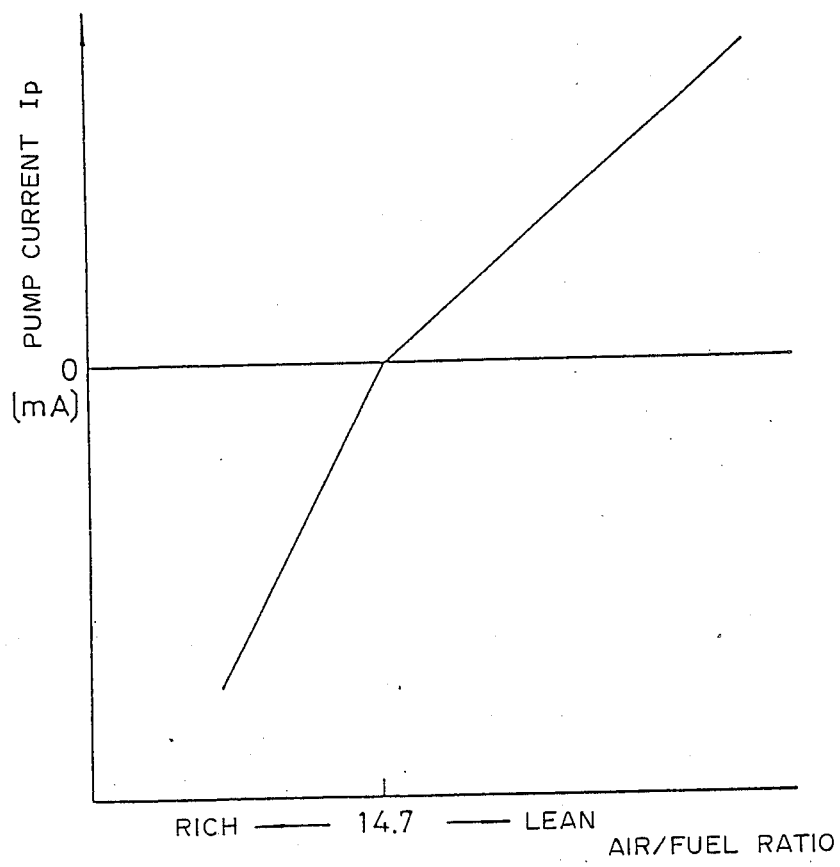
FIG. 4 is an output signal characteristic of the oxygen concentration proportional type oxygen concentration sensor used in the system of FIG. 1.

The voltage Vs exceeds the output voltage from the reference voltage source when the air/fuel ratio of the mixture is in the rich region. Therefore, the output signal level from the differential amplifier 21 turns from the positive level to the negative level. This negative level output signal causes the pump current flowing across the electrodes 16a and 16b of the oxygen pump element 18 to decrease and a change in the direction of the current. Under this condition, the pump current flows from the electrode 16b to the electrode 16a causing he oxygen on the outside to ionize at the electrode 16a and move through the inside of the oxygen pump element 18 to the electrode 16b where the oxygen ion is released into the gas retaining chamber 13 in the form of oxygen gas. Therefore, by supplying the pump current so that the oxygen concentration in the gas retaining chamber 13 is always maintained constant, oxygen is pumped into the gas retaining chamber 13 or pumped out from the gas retaining chamber 13. Therefore, as shown in FIG. 4, the pump current value $I_P$ and the output voltage of the differential amplifier 21 become proportional to the oxygen concentration in the exhaust gas in both of the lean and rich regions. In accordance with this pump current, the above mentioned feedback correction coefficient $K_{O2}$ is determined.

Figure 5A:
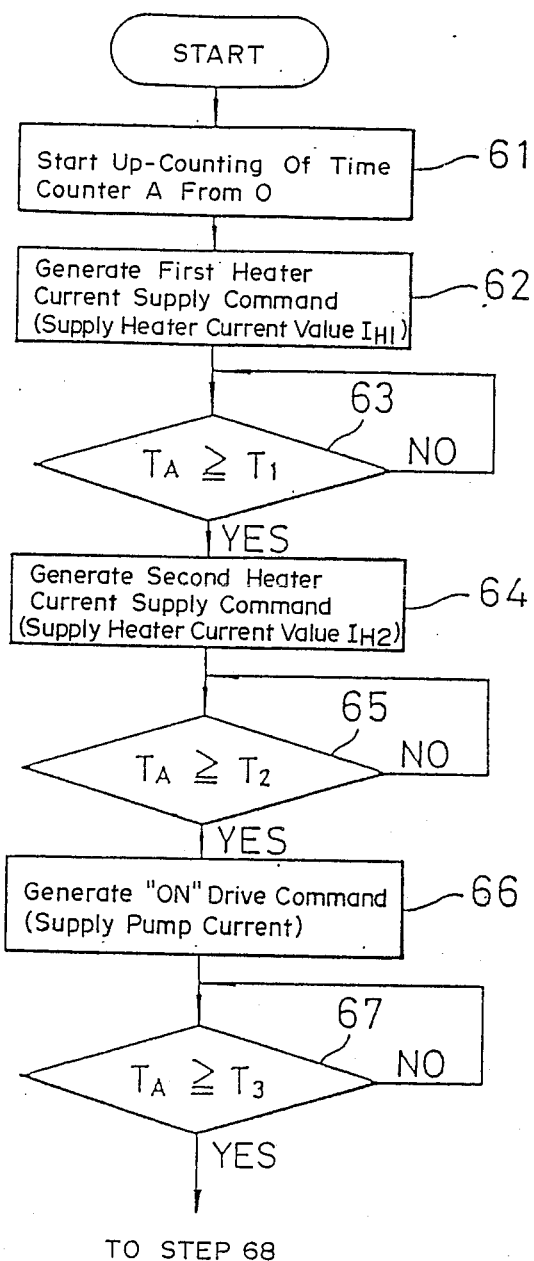
FIGS. 5A and 5B are operational flowcharts showing the manner of operation of the CPU 47 of the system of FIG. 1.
Figure 5B:
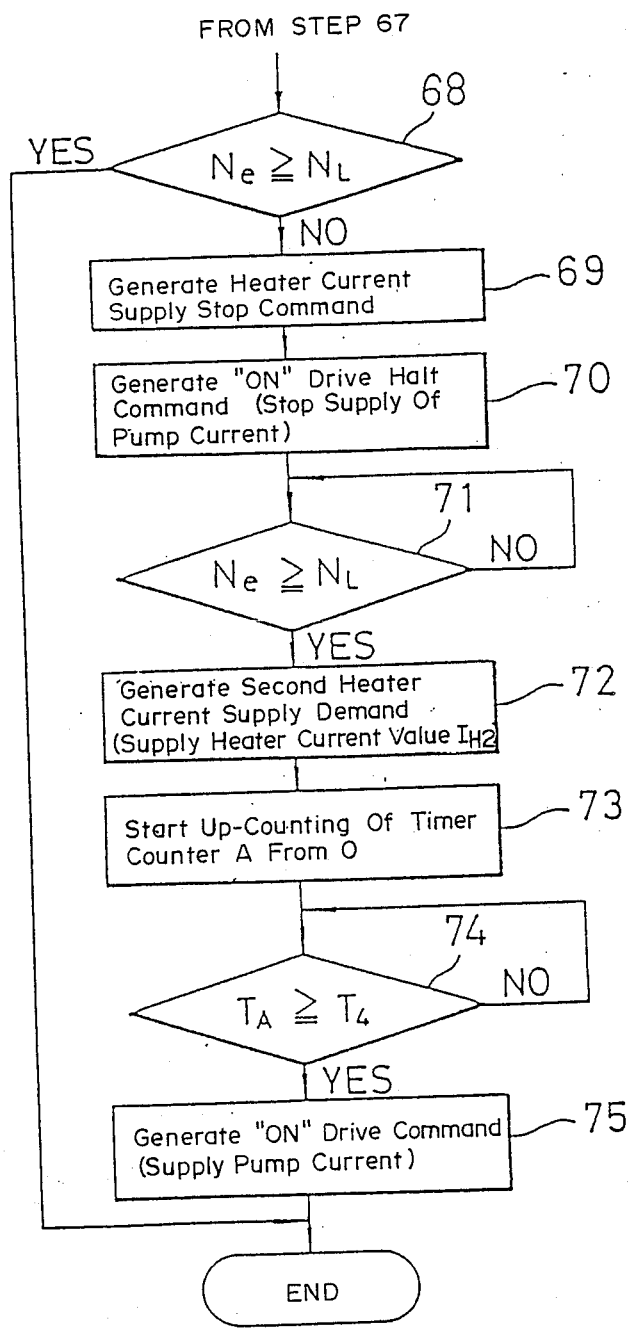

The steps of the air/fuel ratio control method according to the present invention will be explained with reference to the operational flowchart of the CPU 47 which is illustrated in FIGS. 5A and 5B.

In this calculation procedure, the CPU 47 first starts an up-counting operation in a time counter A (not shown) incorporated in the CPU 47 upon closure of the ignition switch 37, in synchronism with a clock pulse signal, at a step 61. Then the CPU 47 supplies a first heater current supply command to the heater current supply circuit 51, at a step 62. In accordance with the first heater current supply command, the heater current supply circuit 51 supplies a heater current having the current value of $I_{H1}$ to the heater element 20, to start the heating of the heater element 20. Next, the CPU determines whether or not a count value $T_A$ of the time counter A has reached a first predetermined time $T_1$ at a step 63. If $T_A \geq T_1$, the CPU 47 supplies a second heater current supply command to the heater current supply circuit 51, at a step 64. In response to the second heater current supply command, the heater current supply circuit 51 supplies a heater current having the current value $I_{H2}$ ($I_{H2} > I_{H1}$) to the heater element 20 to increase the heat generated by the heater element 20. Subsequently, the CPU determines whether or not the count value $T_A$ of the time counter A has reached a second predetermined time period $T_2$ at a step 65. If $T_A \geq T_2$, the CPU 47 supplies an "on" drive command to the drive circuit 46b so that the pump current is supplied to the oxygen pump element 18, at a step 66. After the generation of the "on" drive command, the CPU determines whether or not the count value $T_A$ of the time counter A has reached a third predetermined time period $T_3$ at a step 67. If $T_A \geq T_3$, the CPU determines whether or not the rotational speed of the engine Ne exceeds a predetermined rotational speed $N_L$ at a step 68. If $Ne \geq N_L$, it is determined that the cranking of the engine has been completed and complete combustion is taking place. On the other hand, if $Ne < N_L$, it is determined that the engine has stopped because the rotational speed of the engine Ne has not risen above the predetermined rotational speed $N_L$ although the time period in which the complete combustion of the engine 2 must occur, has lapsed. Therefore, a heater current supply halt command is supplied to the heater current supply circuit 51, at a step 69, and an "on" drive halt command is supplied to the drive circuit 46b, at a step 70. By this operation, the supply of the heater current to the heater element 20 is stopped to prevent the rapid degradation of the oxygen pump element 18 and the sensor cell element 19 by high temperature oxidation, and the switch 27 is turned off, to stop the supply of the pump current to the oxygen pump element 18. Then, the CPU determines whether or not the rotational speed of the engine Ne has reached a speed above the predetermined rotational speed $N_L$ by a restarting of the engine after the engine stall at a step 71. If $Ne \geq N_L$, the second heater current supply command is supplied to the heater current supply circuit 51 at a step 72, and the up-counting operation of the time counter A is started from 0, at a step 73. Then, the CPU determines whether or not the count value $T_A$ of the time counter A has reached a fourth predetermined time period $T_4$ at a step 74. If $TA \geq T_4$, the "on" drive command is supplied to the drive circuit 46b to supply the pump current to the oxygen pump element 18 again, at a step 75.

Figure 6:
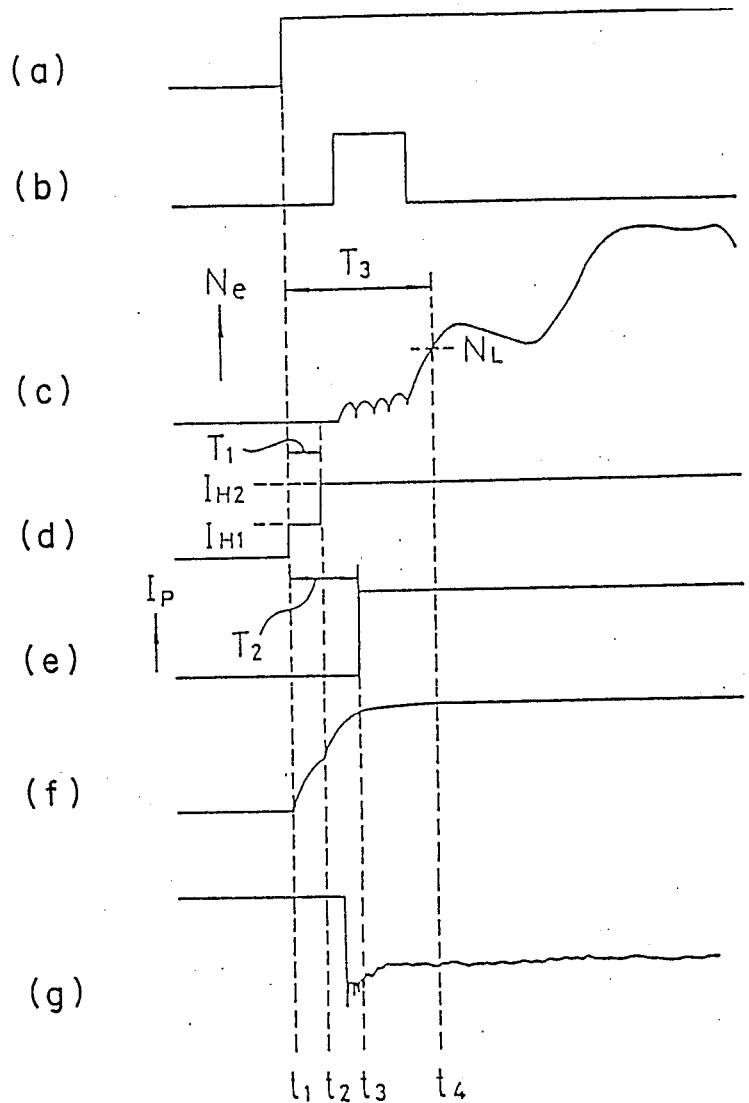
FIG. 6 is a timing chart showing the control operation according to the present invention.

In the method for controlling the oxygen concentration, according to the present invention, as shown in FIG. 6 (d), the heater current having the value $I_{H1}$ is supplied to the heater element 20, as shown in FIG. 6 (d), at the same time of the closing of the ignition switch 37 which is shown to occur at a time $t_1$ in FIG. 6 (a). Then, the heater current having the value of $I_{H2}$ ($I_{H2} > I_{H1}$) is supplied to the heater element 20 starting at the time $t_2$ which is the first predetermined time period $T_1$ after the time point $t_1$. As a result, the heater element 20 generates a maximum amount of heat. On the other hand, after the closing of the ignition switch 37, when a starter switch (not shown) is closed to start the cranking of the engine, the engine rotational speed Ne varies as shown in FIG. 6 (c). At a time point $t_4$ which is the third predetermined time period $T_3$ after the time point $t_1$, the engine speed Ne exceeds the predetermined rotational speed $N_L$. As shown in FIG. 6 (e), the pump current is supplied to the oxygen pump element 18 starting at the time point $t_3$ which is the second predetermined time period $T_2$ after the time point $t_1$. Since the temperature of the oxygen pump element 18 and the sensor cell element 19 raise in such a manner as shown in FIG. 6 (f), the activation of the oxygen concentration sensor completes immediately after the start of the supply of the pump current, so that the air/fuel ratio feedback control is started. Therefore, as shown in FIG. 6 (g), the air/fuel ratio of the mixture supplied to the engine is stabilized at the target air/fuel ratio within a short time after the start of the engine.

In the above described embodiment, the heater current value is raised stepwise after the closing of the ignition switch. However, it should be noted that the manner of raising of the heater current is not limited to this, and for example, it is possible to raise the magnitude of the heater current gradually to the current value $I_{H2}$ within the predetermined time period $T_1$ after the closing of the ignition switch.

Further, in the above described embodiment of the present invention, the air/fuel ratio of the mixture is controlled by adjusting the fuel supply amount in accordance with the pump current value $I_P$. However, besides the above embodiment, it is also possible to apply the method, according to the present invention, to an air/fuel ratio control system of air intake side secondary air supply type, by adjusting the amount of the air intake side secondary air in accordance with the pump current value $I_P$.

Moreover, it is to be noted that almost the same effect as the above explained embodiment can be obtained by reducing the current to the heater element 20 after the closing of the ignition switch 37, for example, until a predetermined engine operation in which the rotational speed of the engine Ne exceeds a predetermined rotational speed $N_1$ ($N_1 < N_L$) is reached, to be lower than the heater current to be supplied after the rotational speed of the engine Ne has raised above the predetermined rotational speed $N_1$.

In view of the foregoing, in the method for controlling an oxygen concentration sensor, according to the present invention, the oxygen pump element and the sensor cell element are gradually heated at the time of a cold start of the engine, by reducing the value of the current to the heater element until the first predetermined time period lapses after the closing of the ignition switch, to be lower than the value of the current to be supplied after the lapse of the first predetermined time period. Therefore, the thermal shock is reduced to prevent the rapid degradation of the oxygen pump element and th sensor cell element. Similarly, the thermal shock can be reduced by reducing the value of the current supplied to the heater element until the predetermined operational state is reached after the closure of the ignition switch, to be lower than the value of the current to be supplied after the predetermined operational state is reached. The rapid degradation of the oxygen pump element and the sensor cell element can be prevented also in this case. Further, since the heating of the pump element and the sensor cell element by the heat of the heater element is started at the same time of the closure of the ignition switch, the temperature of the oxygen concentration sensor can be raised to a level allowing the start of the air/fuel ratio feedback control, within a short time after the complete combustion of the engine is started.

What is claimed is:

1. A method for controlling an oxygen concentration sensor to be used in an internal combustion engine having an ignition switch and an exhaust gas passage, the oxygen concentration sensor having a sensor body forming a gas retaining space which communicates with an inside of the exhaust gas passage through a gas diffusion restriction region and which includes a wall of an oxygen ion conductive solid electrolyte member, the oxygen concentration sensor further having two pairs of electrodes so that each pair is disposed on opposing sides of the wall of the oxygen ion conductive solid electrolyte member and a current source for supplying a current in response to a difference between a voltage developed across one pair of electrodes of the two pairs of electrodes and a reference voltage, the current being supplied to the other pair electrodes of the two pairs of electrodes, the oxygen concentration sensor also having a heater element for generating heat for heating the wall of the oxygen ion conductive solid electrolyte member in accordance with the amount of a heater current supplied thereto, the method comprising the steps of:

measuring time lapsed after the ignition switch of the internal combustion engine is turned on; and controlling a first current value of the heater current, during a first predetermined time period after the ignition switch is turned on, said first current value being smaller than a second current value of the heater current, said second current value being the heater current which is supplied to the heater element after a lapse of said first predetermined time period.

2. The method for controlling an oxygen concentration sensor as set forth in claim 1, further comprising the step of:

controlling the current source of the oxygen concentration sensor to start the supply of the current to the other pair of electrodes when a second predetermined time period has lapsed, said second predetermined time period lapsing after the lapse of said first predetermined time period.

3. A method for controlling an oxygen concentration sensor to be used in an internal combustion engine having an ignition switch and an exhaust gas passage, the oxygen concentration sensor having a sensor body forming a gas retaining space which communicates with an inside of the exhaust gas passage through a gas diffusion restriction region and which includes a wall of an oxygen ion conductive solid electrolyte member, the oxygen concentration sensor further having two pairs of electrodes so that each pair is disposed on opposing sides of the wall of the oxygen ion conductive solid electrolyte member and a current source for supplying a current in response to a difference between a voltage developed across one pair electrodes of the two pairs of electrodes and a reference voltage, the current being supplied to the other pair electrodes of the two pairs of electrodes, the oxygen concentration sensor also having a heater element for generating heat for heating the wall of the oxygen ion conductive solid electrolyte member in accordance with the amount of a heater current supplied thereto, the method comprising the steps of:

detecting an operational state of said internal combustion engine; and controlling a first current value of the heater current, until said operational state of the internal combustion engine detected by said detecting step reaches a predetermined operation state after the ignition switch of the internal combustion engine is turned on, said first current value being smaller than a second current value of the heater current, said second current value being the heater current which is supplied to the heater element after said predetermined operational state is reached.

4. The method for controlling an oxygen concentration sensor as set forth in claim 3, wherein said predetermined operational state is an operation state of the internal combustion engine in which a rotational speed of the internal combustion engine is raised to a speed higher than a predetermined rotational speed.

* * * * *